United States Patent [19]

Misner

[11] Patent Number: 4,777,291
[45] Date of Patent: Oct. 11, 1988

[54] RACEMIZATION PROCESS

[75] Inventor: Jerry W. Misner, Indianapolis, Ind.

[73] Assignee: Eli Lilly and Company, Indianapolis, Ind.

[21] Appl. No.: 706,373

[22] Filed: Feb. 27, 1985

[51] Int. Cl.$^4$ .............................................. C07C 82/00
[52] U.S. Cl. .............................. 564/302; 260/501.18; 564/303; 564/304
[58] Field of Search ................................ 564/302, 303

[56] References Cited

U.S. PATENT DOCUMENTS

| 3,168,566 | 2/1965 | Loter et al. | 564/302 |
| 4,158,016 | 6/1979 | Nagase et al. | 564/302 |
| 4,252,744 | 2/1981 | Bison et al. | 564/302 |

Primary Examiner—Robert V. Hines
Attorney, Agent, or Firm—Bruce J. Barclay; Leroy Whitaker

[57] ABSTRACT

The present invention provides a process for the epimerization of (+)-N-methyl-3-(2-methylphenoxy)-3-phenylpropylamine to its racemic form with an anion forming compound in a suitable solvent.

6 Claims, No Drawings

RACEMIZATION PROCESS

BACKGROUND OF THE INVENTION

Tomoxetine, (−)-N-methyl-3-(2-methylphenoxy)-3-phenylpropylamine, is a valuable compound capable of treating humans suffering from depression. The synthesis currently employed to manufacture tomoxetine produces a racemic mixture which must be resolved to the appropriate (−) isomer.

The resolution of racemic (+−)-N-methyl-3-(2-methylphenoxy)-3-phenylpropylamine produces significant quantities of the undesired (+) isomer. The (+) isomer generally has been discarded because there has been no inexpensive and efficient method of converting it to the desired (−) isomer. The present invention provides a process for epimerizing the (+) isomer to its racemic form, which can then be quickly and economically converted to the desired (−) isomer, tomoxetine.

SUMMARY OF THE INVENTION

The present invention relates to a process for preparing (+−)-N-methyl-3-(2-methylphenoxy)-3-phenylpropylamine of the formula

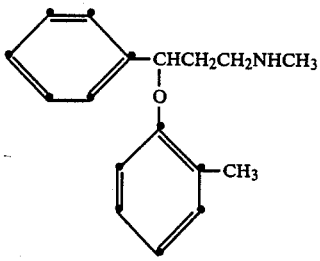

comprising reacting (+)-N-methyl-3-(2-methylphenoxy)-3-phenylpropylamine with an anion forming compound selected from the group consisting of a $C_1$–$C_6$ alkyl alkali metal, $C_1$–$C_6$ alkylamide, alkali metal naphthalene and alkali metal isoprene in a suitable solvent selected from the group consisting of 1,2-dimethoxyethane and tetrahydrofuran under inert conditions.

DETAILED DESCRIPTION OF THE INVENTION

The term "$C_1$–$C_6$ alkyl", as used herein, represents a straight or branched alkyl chain having from one to six carbon atoms. Typical $C_1$–$C_6$ alkyl groups include methyl, ethyl, n-propyl, isopropyl, n-butyl, sec-butyl, n-pentyl, isopentyl, neopentyl, n-hexyl, isohexyl, and the like.

The term "alkali metal", as used herein, represents lithium and sodium.

The anion forming compound employed in the process of the present invention is selected from the group consisting of a $C_1$–$C_6$ alkyl alkali metal, $C_1$–$C_6$ alkylamide, alkali metal naphthalene and alkali metal isoprene. The anion forming compound should be sufficiently basic so as to remove the amine hydrogen atom from (+)-N-methyl-3-(2-methylphenoxy)-3-phenylpropylamine to provide the corresponding anion, and be soluble in the reaction medium. The anion forming compound should not be so strong that it decomposes or degrades the enantiomeric and racemic compounds themselves.

A variety of compounds are suitable anion forming compounds for use in the present process. Preferably, $C_1$–$C_6$ alkylamide and particularly $C_1$–$C_6$ alkyl alkali metal reagents may be employed. Exemplary $C_1$–$C_6$ alkylamides include lithium diethylamide and the like. Typical $C_1$–$C_6$ alkyl alkali metal derivatives include the alkyllithium reagents such as methyllithium, sec-butyllithium and n-butyllithium. Primarily for economic reasons, n-butyllithium is the preferred anion forming compound. Other suitable but less preferred anion forming compounds include alkali metal naphthalenes such as sodium and lithium naphthalenes, as well as alkali metal isoprenes such as sodium and lithium isoprenes.

The quantity of anion forming compound employed in the present process varies depending on the purity of the starting (+) enantiomer. Impurities generally are present with the (+) isomer since the compound is isolated from the mother liquor following resolution of the racemic mixture. Isolation is accomplished by simply evaporating the volatile constituents of the mother liquor following isolation of the desired (−) isomer, typically under reduced pressure. Generally, from about 0.5 molar equivalents to about 1.5 molar equivalents of anion forming compound are employed in the present process for each 1.0 molar equivalent of starting material, with increasing impurities requiring greater amounts of anion forming compound. However, excess anion forming compound may be employed to ensure complete anion formation and is not harmful to the reaction process. As is typical when forming the anion of a compound, the reaction mixture develops a color, for example a pink or reddish hue, and this is generally apparent in the present process as well.

The process of the invention is conducted in a suitable solvent selected from the group consisting of 1,2-dimethoxyethane and especially tetrahydrofuran (THF), which is preferred. When employing THF, the reaction is substantially complete after about 1 to about 5 hours, more typically from about 2 to about 4 hours, when conducted at a temperature in the range of about 15° C. to about 30° C., more typically from about 20° C. to about 25° C. Of course, longer reaction times may be employed if desired, for example when using less preferred anion forming compounds in the process. More generally, longer reaction times may be required for 1,2-dimethoxyethane. For example, the process is typically complete after about 1 to about 40 hours when conducted at a temperature in the range of about −50° C. to about the reflux temperature of the reaction mixture when the reaction is conducted in the presence of 1,2-dimethoxyethane.

The term "inert conditions," as defined herein, refers to the use of a reaction medium exhibiting no chemical activity or that is totally unreactive. Since the anion forming compound is sensitive to both moisture and air, all apparatus may be dried prior to use. Further, the reaction must be conducted under an inert atmosphere, for example, in the presence of argon or especially nitrogen. Finally, all solvents should be thoroughly dried prior to use.

The desired racemic product is readily isolated by routine procedures well known to one of ordinary skill in the art. Water is typically added to the reaction mixture in order to quench any excess anion forming compound which is present. The aqueous solution is extracted with a suitable water immiscible organic solvent such as methylene chloride or chloroform. The organic phase is then concentrated, typically under vacuum, to provide a residue of the racemic product which is suitable for resolution to the desired (−) enantiomer. The residue may be further purified if desired by common techniques such as chromatography over solid supports such as silica gel or alumina or crystallization from common solvents.

Racemic (+−)-N-methyl-3-(2-methylphenoxy)-3-phenylpropylamine thus prepared may be converted to the desired (−) enantiomer by well known procedures used to produce optical isomers. Preferably, the racemate is reacted with L-(+)-mandelic acid to produce the salt of the (−) isomer, which readily crystallizes. Typically, 0.5 molar equivalents of L-(+)-mandelic acid is combined with 1.0 molar equivalent of the racemic compound in a mutual solvent. Exemplary mutual solvents include the ethers such as diethyl ether or tetrahydrofuran; the aliphatic hydrocarbons such as hexane, pentane and the like; aromatic hydrocarbons such as benzene, toluene and xylene; the alcohols such as methanol or ethanol; esters such as ethyl acetate; halogenated hydrocarbons such as methylene chloride or chloroform; and other like protic and aprotic solvents. The reaction is substantially complete after about 1 to about 24 hours when conducted at a temperature in the range of about 0° C. to about the reflux temperature of the reaction mixture. The product thus prepared may be isolated by standard procedures.

The compound thus prepared is preferably converted to the hydrochloride salt prior to its use as a pharmaceutical agent. This compound is prepared by well known procedures. Typically, the mandelic acid salt is converted to the free amine by reaction with a suitable base such as sodium hydroxide. The free amine is then dissolved in a suitable solvent and combined with hydrochloric acid, either in gaseous form, or preferably an aqueous solution. Tomoxetine hydrochloride thus prepared may be isolated according to standard procedures such as crystallization from common solvents.

The present process permits the use of previously discarded (+) isomer generated in the resolution of racemic (+−)-N-methyl-3-(2-methylphenoxy)-3-phenylpropylamine. As such, the present process would be particularly useful in a production setting in the form of a continuous process whereby the (+) isomer generated in the resolution process may be converted to the racemic mixture which is then combined with the racemic mixture material prepared by the currently employed manufacturing procedure for that compound. Further, the present process does not require complete conversion of the (+) isomer to the racemic mixture since subsequent resolution of the racemic mixture would merely generate additional (+) isomer which can be racemized to the racemic mixture in continuous fashion by the present process.

Tomoxetine and salts thereof are known pharmaceuticals useful for the treatment of a variety of human disorders. See, e.g., U.S. Patent Nos. 4,314,081, 4,018,895, and 4,194,009, all incorporated herein by reference, for a discussion of the use of the compounds disclosed therein as psychotropic agents, and in particular their use as antidepressants.

The following Examples illustrate the synthesis of (+−)-N-methyl-3-(2-methylphenoxy)-3-phenylpropylamine according to the process of the present invention. The Examples are not intended to be limiting in any respect and should not be so construed.

As is known, a mixture of equal parts of enantiomers is a racemic mixture. A racemic mixture is optically inactive since the rotation caused by a molecule of one isomer is exactly canceled by an equal and opposite rotation caused by a molecule of its enantiomer. As such, the formation of the racemic mixture prepared by the present process is measured by its specific rotation. Specific rotations approaching zero degrees are indicative of a racemic mixture.

EXAMPLE 1

(+−)-N-Methyl-3-(2-methylphenoxy)-3-phenylpropylamine

A 50 ml 3-neck round bottom flask fitted with a gas inlet tube, thermometer and addition funnel was charged with 1.51 g of residue containing 1.27 g (5.0 mmol) of (+)-N-methyl-3-(2-methylphenoxy)-3-phenylpropylamine and 20 ml of dry THF. Nitrogen gas was bubbled subsurface during the reaction process. Using an external cold water bath to maintain the temperature of the reaction mixture between about 17° C. and 22° C., 2.3 ml (5.25 mmol) of 2.3M n-butyllithium in hexane (Aldrich Chemical Company, Milwaukee, Wis.) was added dropwise to the reaction mixture over a period of about five minutes. The reaction mixture was stirred at room temperature for about 3½ hours. The mixture was diluted by the addition of 25 ml of water. The aqueous solution was extracted with 25 ml of methylene chloride and the organic phase was separated, dried over anhydrous sodium sulfate and evaporated under vacuum to provide 1.24 g of (+−)-N-methyl-3-(2-methylphenoxy)-3-phenylpropylamine as an oil. Yield 97%.

| $[\alpha]_{589}^{25°C.} = 0°$ | $[\alpha]_{365}^{25°C.} = +1.2°$ |
| --- | --- | concentration=1% in methanol

EXAMPLE 2

(+−)-N-Methyl-3-(2-methylphenoxy)-3-phenylpropylamine

A 1 l. 3-neck round bottom flask equipped with a gas inlet tube, thermometer and addition funnel was placed in an external ice/water bath and charged with 56.74 g of residue containing 51.0 g (0.2 mol) of (+)-N-methyl-3-(2-methylphenoxy)-3-phenylpropylamine and 350 ml of dry THF under a nitrogen atmosphere. To this solution was added 91.3 ml (0.21 mol) of 2.3M n-butyllithium in hexane dropwise over a period of approximately 45 minutes while maintaining the temperature of the reaction mixture between about 15° C. and 20° C. The ice/water bath was removed and the reaction mixture was stirred at room temperature for approximately 3 hours. The reaction mixture was cooled to approximately 15° C. with an external ice/water bath and 3 ml of water was added to the mixture. Following the resulting exotherm, 350 ml of water was added to the mixture. Next, 350 ml of methylene chloride was added to the mixture and the organic layer was separated. The flask was washed with 100 ml of methylene chloride and the organic phases were combined and filtered through anhydrous sodium sulfate to provide 47.85 g of racemic (+−)-N-methyl-3-(2-methylphenoxy)-3-phenylpropylamine following evaporation of the solvent under reduced pressure. Yield 94%. GLC indicated 92.5% pure product.

| $[\alpha]_{589}^{25°C.} = +1.8°$ | $[\alpha]_{365}^{25°C.} = +8.2°$ | concentration=1% in methanol

EXAMPLE 3

(+−)-N-Methyl-3-(2-methylphenoxy)-3-phenyl-propylamine

A 50 ml 3-neck round bottom flask equipped with a nitrogen inlet tube, thermometer and addition funnel was placed in a dry ice/acetone bath and charged with 1.27 g (5.0 mmol) of (+)-N-methyl-3-(2-methylphenoxy)-3-phenylpropylamine and 25 ml of dry THF under a nitrogen atmosphere. The resulting solution was cooled to −72° C. and 2.5 ml (5.4 mmol) of 2.3M n-butyllithium in hexane was added over a period of approximately 15 minutes while maintaining the temperature of the reaction mixture below approximately −65° C. The reaction mixture was warmed to approximately 20° C. and stirred at that temperature for a period of about 3 hours. The reaction mixture was charged with 25 ml of water and 25 ml of methylene chloride. The organic phase was separated, filtered through anhydrous sodium sulfate and evaporated under vacuum to provide 1.14 g of the racemic product as an oil. Yield 90%.

| $[\alpha]_{589}^{25°C.} = +0.60°$ | $[\alpha]_{365}^{25°C.} = +2.2°$ | concentration=1% in methanol

EXAMPLE 4

(+−)-N-Methyl-3-(2-methylphenoxy)-3-phenyl-propylamine

A 50 ml 3-neck round bottom flask equipped with a gas inlet tube, thermometer and addition funnel was charged with 1.51 g of residue containing 1.27 g (5.0 mmol) of (+)-N-methyl-3-(2-methylphenoxy)-3-phenylpropylamine and 20 ml of dry 1,2-dimethoxyethane under a nitrogen atmosphere. To this mixture was added 2.3 ml (5.25 mmol) of 2.3M n-butyllithium in hexane over a period of approximately 6 minutes. . The reaction mixture was stirred at room temperature overnight and 25 ml of water was added thereto. The product was extracted with 25 ml of chloroform and the organic phase was filtered through anhydrous sodium sulfate. The filtrate was evaporated to dryness under reduced pressure to provide 1.27 g of (+−)-N-methyl-3-(2-methylphenoxy)-3-phenylpropylamine as an oil. Yield 100%.

| $[\alpha]_{589}^{25°C.} = +0.4°$ | $[\alpha]_{365}^{25°C.} = +2.2°$ | concentration=1% in methanol.

EXAMPLE 5

(+−)-N-Methyl-3-(2-methylphenoxy)-3-phenyl-propylamine

A 50 ml 3-neck round bottom flask equipped with a gas inlet tube, thermometer and addition funnel was charged with 1.27 g (5.0 mmol) of (+)-N-methyl-3-(2-methylphenoxy)-3-phenylpropylamine and 25 ml of dry THF at room temperature under a nitrogen atmosphere. To this mixture was added 5.0 ml (5.5 mmol) of 1.1M sec-butyllithium in cyclohexane over a period of approximately 15 minutes. During this period the reaction mixture temperature increased from 21° to 26° C. The reaction mixture was stirred at room temperature for approximately 2 hours and 25 ml of water was added to the mixture. The product was isolated by extraction of the reaction mixture with 25 ml of methylene chloride. Following separation the organic phase was filtered through anhydrous sodium sulfate and evaporated under vacuum to provide 1.17 g of (+−)-N-methyl-3-(2-methylphenoxy)-3-phenylpropylamine. Yield 92%.

| $[\alpha]_{589}^{25°C.} = +0.4°$ | $[\alpha]_{365}^{25°C.} = +3.59°$ | concentration=1% in methanol

EXAMPLE 6

(+−)-N-Methyl-3-(2-methylphenoxy)-3-phenyl-propylamine

A solution of 1.27 g (5.0 mmol) of (+)-N-methyl-3-(2-methylphenoxy)-3-phenylpropylamine and 25 ml of dry THF in a 50 ml 3-neck round bottom flask fitted with a thermometer and gas inlet tube was cooled to −72° C. under a nitrogen atmosphere. To this mixture was added 5.0 ml (5.5 mmol) of sec-butyllithium in cyclohexane and the reaction mixture was allowed to warm to a temperature of approximately 19° C. Four hours following the addition of the sec-butyllithium the reaction mixture was quenched with 1 ml of water. Following the exotherm an additional 25 ml of water and 25 ml of methylene chloride was added to the reaction mixture. The organic layer was separated and filtered through anhydrous sodium sulfate to provide 1.17 g of (+−)-N-methyl-3-(2-methylphenoxy)-3-phenylpropylamine following evaporation of the volatile constituents under reduced pressure. Yield 92%.

| $[\alpha]_{589}^{25°C.} = -0.19°$ | $[\alpha]_{365}^{25°C.} = +0.78°$ | concentration=1% in methanol

EXAMPLE 7

(+−)-N-Methyl-3-(2-methylphenoxy)-3-phenyl-propylamine

Diisopropylamine (0.56 g, 5.5 mmol) was dissolved in 15 ml of THF under nitrogen in a 50 ml 3-neck round bottom flask fitted with a gas inlet tube, thermometer and addition funnel. The solution was cooled to about −70° C. and 2.4 ml (5.5 mmol) of 2.3M n-butyllithium in hexane was added over a period of approximately 5 minutes while maintaining the temperature of the reaction mixture below about −65° C. The mixture was stirred for 5 minutes. To this mixture was added a solution of 1.27 g (5.0 mmol) of (+)-N-methyl-3-(2-methylphenoxy)-3-phenylpropylamine dissolved in 5 ml of dry THF dropwise over a period of approximately 10 minutes while maintaining the temperature of the reaction mixture below approximately −65° C. The reaction mixture was stirred for about 5 minutes and the mixture was allowed to warm to room temperature, approximately 20° C., over a period of about 3½ hours. The reaction mixture was quenched with 20 ml of water and the mixture was extracted with 25 ml of methylene chloride. The organic phase was isolated and filtered through anhydrous sodium sulfate, and the resulting filtrate was concentrated under vacuum to dryness to provide 1.18 g of (+ −)-N-methyl-3-(2-methylphenoxy)-3-phenylpropylamine. Yield 93%.

$$[\alpha]_{589}^{25°C} = +0.8°$$

concentration=1% in methanol

EXAMPLE 8

(+ −)-N-Methyl-3-(2-methylphenoxy)-3-phenylpropylamine

A 50 ml 3-neck round bottom flask fitted with a gas inlet tube, thermometer and addition funnel was charged with 1.42 g of a residue containing 1.27 g (5.0 mmol) of (+)-N-methyl-3-(2-methylphenoxy)-3-phenylpropylamine and 20 ml of dry THF under nitrogen. While maintaining the temperature of the reaction mixture between about 15° C. and 20° C., 3.7 ml (5.5 mmol) of 1.5M methyllithium in diethyl ether was added dropwise to the solution over a period of about 5 minutes. The reaction mixture was stirred at room temperature for about 3½ hours and quenched with 25 ml of water. The product was isolated by extraction of the mixture with 25 ml of methylene chloride. The organic phase was separated, dried over anhydrous sodium sulfate and concentrated under vacuum to provide 1.13 g of (+ −)-N-methyl-3-(2-methylphenoxy)-3-phenylpropylamine as an oil. Yield 89%.

$$[\alpha]_{589}^{25°C} = +2.58° \qquad [\alpha]_{365}^{25°C} = +4.37°$$

concentration=1% in methanol.

EXAMPLE 9

(+ −)-N-Methyl-3-(2-methylphenoxy)-3-phenylpropylamine

Diethylamine (0.38 g, 5.25 mmol) was dissolved in 15 ml of dry THF under nitrogen in a 50 ml 3-neck round bottom flask equipped with a gas inlet tube and thermometer. The resulting yellow solution was cooled to approximately −75° C. with an external dry ice/acetone bath. To this solution was added 23 ml (5.25 mmol) of 2.3 M n-butyllithium in hexane dropwise while maintaining the temperature of the reaction mixture below about −65° C. The reaction mixture was stirred for about 5 minutes whereupon a solution of 1.42 g of residue containing 1.27 g (5.0 mmol) of (+)-N-methyl-3-(2-methylphenoxy)-3-phenylpropylamine dissolved in 15 ml of dry THF was added dropwise over a period of about 20 minutes while maintaining the temperature below about −65° C. The reaction mixture was allowed to warm to room temperature over a 3½ hour period and 25 ml of water was added thereto. The mixture was extracted with 25 ml of methylene chloride and the resulting organic phase was filtered through anhydrous sodium sulfate. Following evaporation of the organic phase under reduced pressure, 1.24 g of the title compound was isolated as an oil. Yield 98%.

$$[\alpha]_{589}^{25°C} = +0.6° \qquad [\alpha]_{365}^{25°C} = +2.4°$$

concentration=1% in methanol

EXAMPLE 10

(+ −)-N-Methyl-3-(2-methylphenoxy)-3-phenylpropylamine

A 50 ml 3-neck round bottom flask equipped with a thermometer, gas inlet tube, and addition funnel was placed in an ice/acetone bath and charged with 1.42 g of residue containing 1.27 g (5.0 mmol) of (+)-N-methyl-3-(2-methylphenoxy)-3-phenylpropylamine and 18 ml of dry THF under nitrogen. Sodium metal (0.12 g, 5.0 mmol) and 0.5 ml (0.34 g, 5.0 mmol) of isoprene in 2 ml of THF were next added to the reaction mixture, and the external ice bath was removed. The reaction mixture was stirred at room temperature overnight. The reaction mixture was quenched with 25 ml of water and extracted with 25 ml of methylene chloride. The organic phase was dried over anhydrous sodium sulfate and concentrated under vacuum to provide 1.27 g of racemic (+ −)-N-methyl-3-(-2-methylphenoxy)-3phenylpropylamine as an oil. Yield 100%.

$$[\alpha]_{589}^{25°C} = +3.61° \qquad [\alpha]_{365}^{25°C} = +19.06°$$

While substantial racemization had occurred, the reaction appeared not to have been completed.

EXAMPLE 11

(+ −)-N-Methyl-3-(2-methylphenoxy)-3-phenylpropylamine

A 50 ml 3-neck round bottom flask equipped with a nitrogen inlet tube, thermometer and addition funnel was charged with 1.42 g of a residue containing 1.27 g (5.0 mmol) of (+)-N-methyl-3-(2-methylphenoxy)-3-phenylpropylamine and 20 ml of dry THF under nitrogen. To this solution was added 0.12 g (5.0 mmol) of sodium metal and 0.64 g (5.0 mmol) of naphthalene. The reaction mixture was stirred overnight at room temperature. The mixture was quenched with 25 ml of water and extracted with 25 ml of methylene chloride. The organic phase was separated, dried over anhydrous sodium sulfate and concentrated under vacuum to provide 1.71 g of an oil. In order to remove the residual naphthalene, the oil was dissolved in 30 ml of diethyl ether. The organic phase was extracted with 20 ml of 4N hydrochloric acid and the pH of the acidic aqueous solution was raised to about 9 with 5N sodium hydroxide. The basic aqueous solution was extracted with diethyl ether and the organic phase was separated, dried over anhydrous sodium sulfate and concentrated under vacuum to dryness to provide 0.88 g of (+ −)-N-methyl-3-(2-methylphenoxy)-3-phenylpropylamine as an oil. Yield 69%.

$[\alpha]^{25°C}_{589} = +2.00°$ concentration=1% in methanol

EXAMPLE 12

(+ −)-N-Methyl-3-(2-methylphenoxy)-3-phenylpropylamine

A 50 ml 3-neck round bottom flask equipped with a nitrogen inlet tube, thermometer and addition funnel was charged with 1.42 g of a residue containing 1.27 g (5.0 mmol) of (+)-N-methyl-3-(2-methylphenoxy)-3-phenylpropylamine and 20 ml of dry THF under nitrogen. To this solution was added 0.04 g (5.7 mmol) of lithium metal and 0.64 g (5.0 mmol) of naphthalene. The reaction mixture was stirred overnight at room temperature. The mixture was quenched with 25 ml of water and extracted with 25 ml of methylene chloride. The organic phase was separated, dried over anhydrous sodium sulfate and concentrated under vacuum to provide 1.71 g of an oil. In order to remove the residual naphthalene, the oil was dissolved in 30 ml of diethyl ether. The organic phase was extracted with 20 ml of 4N hydrochloric acid and the pH of the acidic aqueous solution was raised to about 9 with 5N sodium hydroxide. The basic aqueous solution was extracted with diethyl ether and the organic phase was separated, dried over anhydrous sodium sulfate and concentrated under vacuum to dryness to provide 0.93 g of (+ −)-N-methyl-3-(2-methylphenoxy)-3-phenylpropylamine as an oil. Yield 73%.

$[\alpha]^{25°C.}_{589} = 0°$ concentration=1% in methanol

EXAMPLE 13

(+ −)-N-Methyl-3-(2-methylphenoxy)-3-phenylpropylamine

A 1 l. 3-neck round bottom flask fitted with a gas inlet tube, thermometer and addition funnel was placed in an ice/acetone bath and charged with 38.3 g (0.15 mol) of (+)-N-methyl-3-(2-methylphenoxy)-3-phenylpropylamine and 250 ml of dry THF under a nitrogen atmosphere. The resulting mixture was cooled to approximately −5° C. whereupon 145 ml (0.16 mol) of 1.1M sec-butyllithium in cyclohexane was added dropwise while maintaining the temperature of the mixture below approximately 5° C. The addition was accomplished in about 15 minutes. Following the addition of the anion forming compound the external cooling bath was removed and the reaction mixture was stirred for about 3 hours to a temperature of about 20° C. The reaction mixture was quenched by addition of 25 ml of water. An additional 225 ml of water and 250 ml of methylene chloride were added to the reaction mixture. The organic phase was separated and filtered through anhydrous sodium sulfate. The volatiles were evaporated under vacuum at a temperature of about 62° C. for 1 hour to provide 34.3 g of (+ −)-N-methyl-3-(2-methylphenoxy)-3-phenylpropylamine as an oil. Yield 90%.

| $[\alpha]^{25°C.}_{589} = +0.0°$ | $[\alpha]^{25°C.}_{365} = +1.59°$ |
| --- | --- | concentration=1% in methanol

The following example illustrates the resolution of the racemic mixture isolated above to tomoxetine.

(−)-N-Methyl-3-(2-methylphenoxy)-3-phenylpropylamine mandelic acid

To a solution of 33.69 g (0.132 mol) of (+ −)-N-methyl-3-(2-methylphenoxy)-3-phenylpropylamine dissolved in 50 ml of diethyl ether was added a solution of 9.89 g (0.067 mol) of L-(+)-mandelic acid in 20 ml of warm xylene. The resulting mixture was refluxed gently for about 5 minutes and an additional 30 ml of diethyl ether was added thereto. The mixture was stirred at room temperature overnight and the resulting slurry was chilled in an ice bath. The mixture was filtered and the resulting solid was rinsed with 50 ml of diethyl ether. The solid was dissolved in 25 ml of methylene chloride and 50 ml of ethyl acetate and the resulting mixture was heated to reflux. The methylene chloride was removed by vacuum and 50 ml of diethyl ether was added to the residue. The mixture was seeded with a crystal of desired product and the resulting mixture was stirred for 2 hours while being chilled in an ice bath. The precipitated solid was collected by filtration and rinsed with 30 ml of a 1:1 (v:v) ethyl acetate/diethyl ether solvent solution. The resulting solid was dried overnight at 55° C. in a vacuum oven to provide 15.7 g of (−)-N-methyl-3-(2-methylphenoxy)-3-phenylpropylamine mandelic acid as an off white solid. mp =119°-122° C. The resulting solid was recrystallized with 50 ml of methanol employing 3 g of decolorizing carbon. The resulting mixture was filtered through Celite and the filtrate was concentrated under vacuum to provide a white solid. This solid was dissolved in 50 ml of ethyl acetate with heating and the solution was allowed to cool. An additional 50 ml of diethyl ether was added and the precipitated solid was collected by filtration and rinsed with 50 ml of 1:1 (v:v) ethyl acetate/diethyl ether. The solid was dried in a vacuum oven at 50° C. for 1 hour to provide 13.2 g of (−)-N-methyl-3-(2-methylphenoxy)-3-phenylpropylamine mandelic acid. mp=122°-123° C. Yield 49%.

Tomoxetine Hydrochloride (−)-N-Methyl-3-(2-methylphenoxy)-3-phenylpropylamine mandelic acid (13.2 g, 0.032 mol) was dissolved in 50 ml of 2N sodium hydroxide and 50 ml of diethyl ether. The organic phase was separated, filtered over anhydrous sodium sulfate and concentrated under vacuum to provide 6.85 g of a pale yellow liquid. This liquid was dissolved in 35 ml of ethyl acetate and the resulting solution was saturated with anhydrous hydrochloric acid gas. The resulting mixture was stirred in an ice bath for 30 minutes and the precipitated solid was collected by filtration. The solid was rinsed with 20 ml of ethyl acetate and dried in a vacuum oven at 55° C. to provide 8.17 g of tomoxetine hydrochloride. Yield 62.7%. mp =160°-162° C.

| $[\alpha]^{25°C.}_{589} = -30.71°$ | $[\alpha]^{25°C.}_{365} = -140.58°$ |
| --- | --- | concentration=1% in methanol

I claim:

1. A process for preparing (+ −)-N-methyl-3-(2-methylphenoxy)-3-phenylpropylamine of the formula

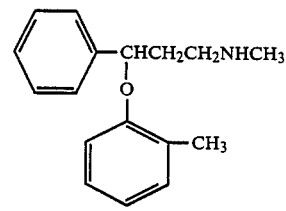

comprising reacting (+)-N-methyl-3-(2-methylphenoxy)-3-phenylpropylamine with an anion forming compound selected from the group consisting of a $C_1$–$C_6$ alkyl alkali metal and $C_1$–$C_6$ alkyl amide in a suitable solvent selected from the group consisting of 1,2-dimethoxyethane and tetrahydrofuran under inert conditions wherein from about 0.5 molar equivalents to about 1.5 molar equivalents of an anion forming compound are employed for each 1.0 molar equivalent of (+−)-N-methyl-3-(2-methylphenoxy)-3-phenyl-propylamine.

2. A process of claim 1 wherein the suitable solvent is tetrahydrofuran.

3. A process of claim 2 wherein the anion forming compound is a $C_1$–$C_6$ alkyl alkali metal.

4. A process of claim 3 wherein the $C_1$–$C_6$ alkyl alkali metal is a $C_1$–$C_6$ alkyllithium.

5. A process of claim 4 wherein the $C_1$–$C_6$ alkyllithium compound is n-butyllithium.

6. A process of claim 4 wherein the $C_1$–$C_6$ alkyllithium compound is sec-butyllithium.

* * * * *